(12) United States Patent
Selbach et al.

(10) Patent No.: US 10,140,881 B1
(45) Date of Patent: Nov. 27, 2018

(54) CPR TRAINING ASSEMBLY (71) Applicants: Dave Selbach, Palm Harbor, FL (US); Jennifer Geston-Selbach, Palm Harbor, FL (US)

(72) Inventors: Dave Selbach, Palm Harbor, FL (US); Jennifer Geston-Selbach, Palm Harbor, FL (US)

( * ) Notice: Subject to any disclaimer, the term of this patent is extended or adjusted under 35 U.S.C. 154(b) by 0 days.

(21) Appl. No.: 15/947,561

(22) Filed: Apr. 6, 2018

(51) Int. Cl.
*A61N 1/39* (2006.01)
*G09B 5/04* (2006.01)
*G09B 23/28* (2006.01)
*A61M 16/00* (2006.01)

(52) U.S. Cl.
CPC ............. *G09B 5/04* (2013.01); *G09B 23/288* (2013.01); *A61H 2201/5043* (2013.01); *A61H 2201/5048* (2013.01); *A61M 16/0048* (2013.01)

(58) Field of Classification Search
CPC ........... G06F 3/167; G09B 23/30; G09B 5/04; G09B 5/06; G09B 23/288; A61B 5/4848; A61H 2201/5043; A61H 2201/5048; A61M 16/0048; A61N 1/3912; A61N 1/3993; A61N 1/3987
See application file for complete search history.

(56) References Cited

U.S. PATENT DOCUMENTS

| 5,913,685 A | 6/1999 | Hutchins |
| 8,837,683 B2 | 9/2014 | Conroy |
| 9,173,807 B2 * | 11/2015 | Freeman .............. A61H 31/005 |
| 9,352,166 B2 | 5/2016 | Sullivan et al. |
| 9,370,462 B2 | 6/2016 | Halsne |
| 9,375,381 B2 * | 6/2016 | Freeman .............. A61H 31/005 |
| D772,298 S | 11/2016 | Carreon |
| 9,498,152 B2 * | 11/2016 | Bowers .............. A61B 5/02055 |
| 9,522,096 B2 * | 12/2016 | Jensen ................. A61H 31/005 |
| 9,788,734 B2 * | 10/2017 | Tan ..................... A61H 31/005 |
| 2002/0007832 A1 * | 1/2002 | Doherty .............. A61H 31/005 128/202.29 |
| 2005/0267536 A1 * | 12/2005 | Freeman ................ A61N 1/046 607/5 |
| 2006/0262946 A1 * | 11/2006 | Yang ...................... H04R 5/027 381/175 |
| 2008/0081321 A1 | 4/2008 | Cantrell et al. |
| 2012/0100516 A1 * | 4/2012 | Iwami .................. G09B 23/288 434/265 |
| 2014/0072940 A1 * | 3/2014 | Wood .................. G09B 23/288 434/265 |

(Continued)

FOREIGN PATENT DOCUMENTS

WO WO2016007471 1/2016

*Primary Examiner* — An T Nguyen (57) ABSTRACT

A CPR training assembly for instructing a person to perform CPR or choking rescue on an infant, a child or an adult includes a housing and an audio unit that is coupled to the housing. The audio unit emits audio outwardly from the housing to audibly alert a user. The audio unit stores data pertaining to audible instructions for performing CPR or choking rescue on infants, children and adults. A control unit is coupled to the housing and the control unit is electrically coupled to the audio unit to select the audible instructions for a respective one of the infants, children and adults. In this way the user can choose to receive audible instructions that correspond to whether an infant, a child or an adult needs CPR or choking rescue.

11 Claims, 5 Drawing Sheets

(56) References Cited

U.S. PATENT DOCUMENTS

| | | | |
|---|---|---|---|
| 2015/0031961 A1* | 1/2015 | Freeman | G09B 23/288 |
| | | | 600/300 |
| 2016/0004931 A1 | 1/2016 | Carlson | |
| 2017/0076634 A1* | 3/2017 | Hoss | G09B 23/288 |
| 2017/0252571 A1* | 9/2017 | Dascoli | A61N 1/39044 |

* cited by examiner

CPR TRAINING ASSEMBLY

CROSS-REFERENCE TO RELATED APPLICATIONS

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to training devices and more particularly pertains to a new training device for instructing a person to perform CPR or choking rescue on an infant, a child or an adult.

BRIEF SUMMARY OF THE INVENTION

An embodiment of the disclosure meets the needs presented above by generally comprising a housing and an audio unit that is coupled to the housing. The audio unit emits audio outwardly from the housing to audibly alert a user. The audio unit stores data pertaining to audible instructions for performing CPR or choking rescue on infants, children and adults. A control unit is coupled to the housing and the control unit is electrically coupled to the audio unit to select the audible instructions for a respective one of the infants, children and adults. In this way the user can choose to receive audible instructions that correspond to whether an infant, a child or an adult needs CPR or choking rescue.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
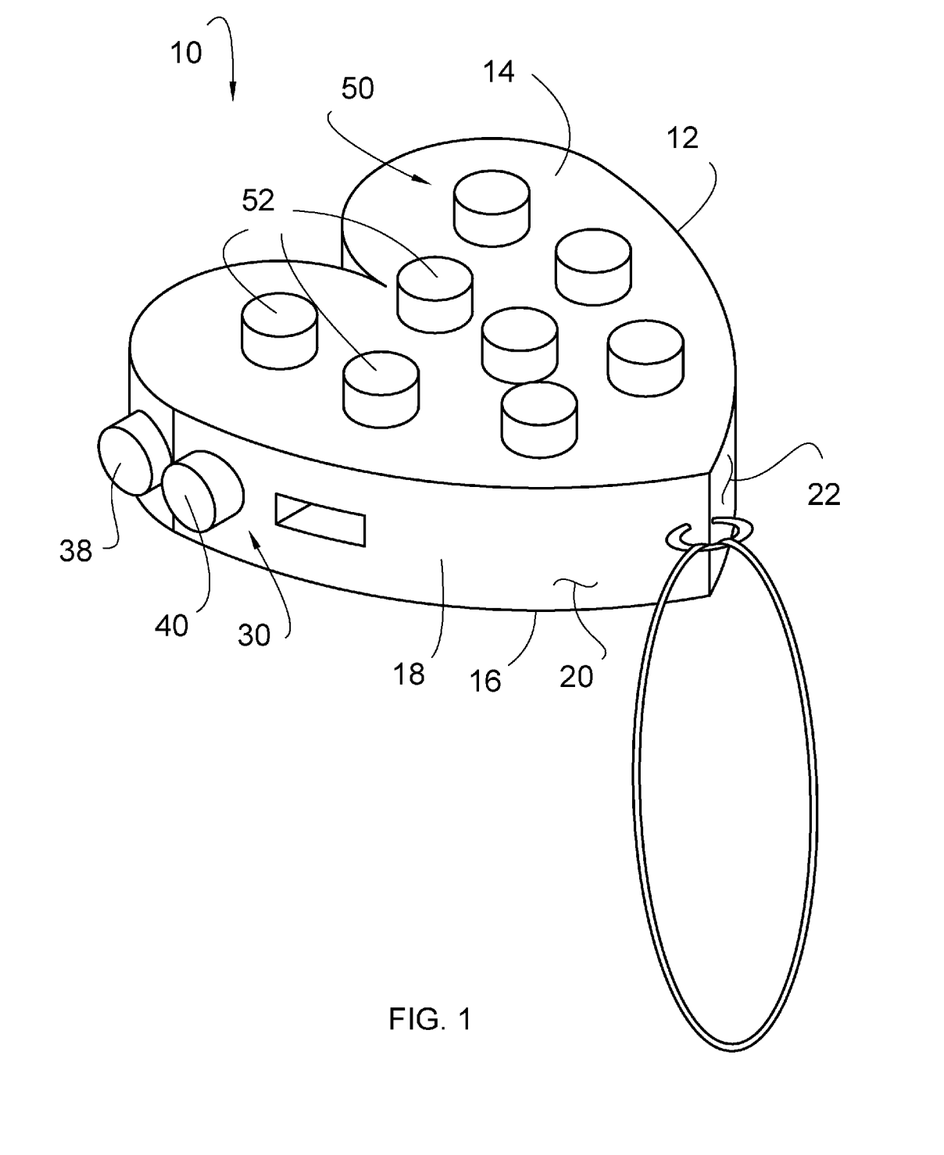
FIG. 1 is a top perspective view of a CPR training assembly according to an embodiment of the disclosure.
Figure 2:
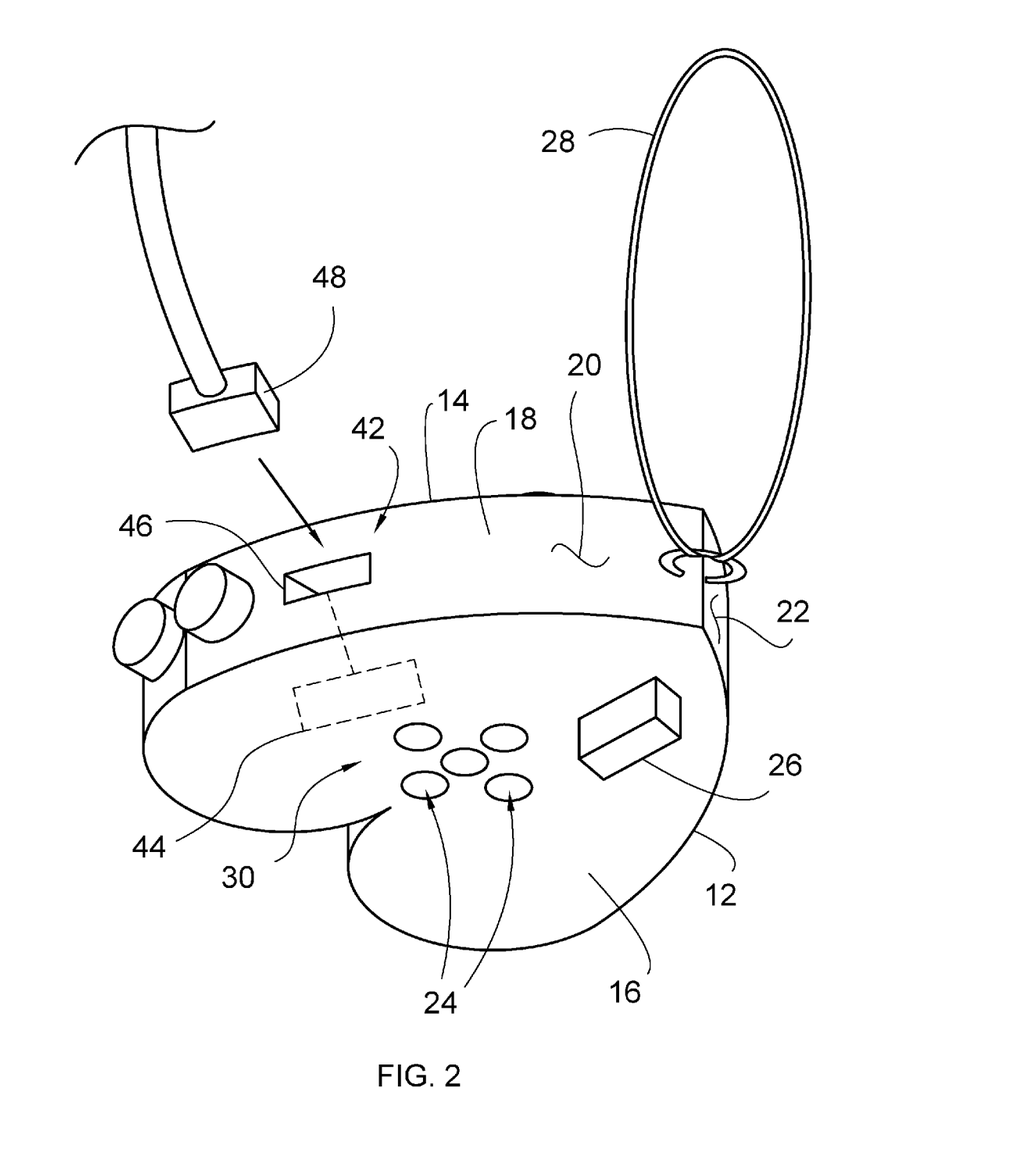
FIG. 2 is a bottom perspective view of an embodiment of the disclosure.
Figure 3:
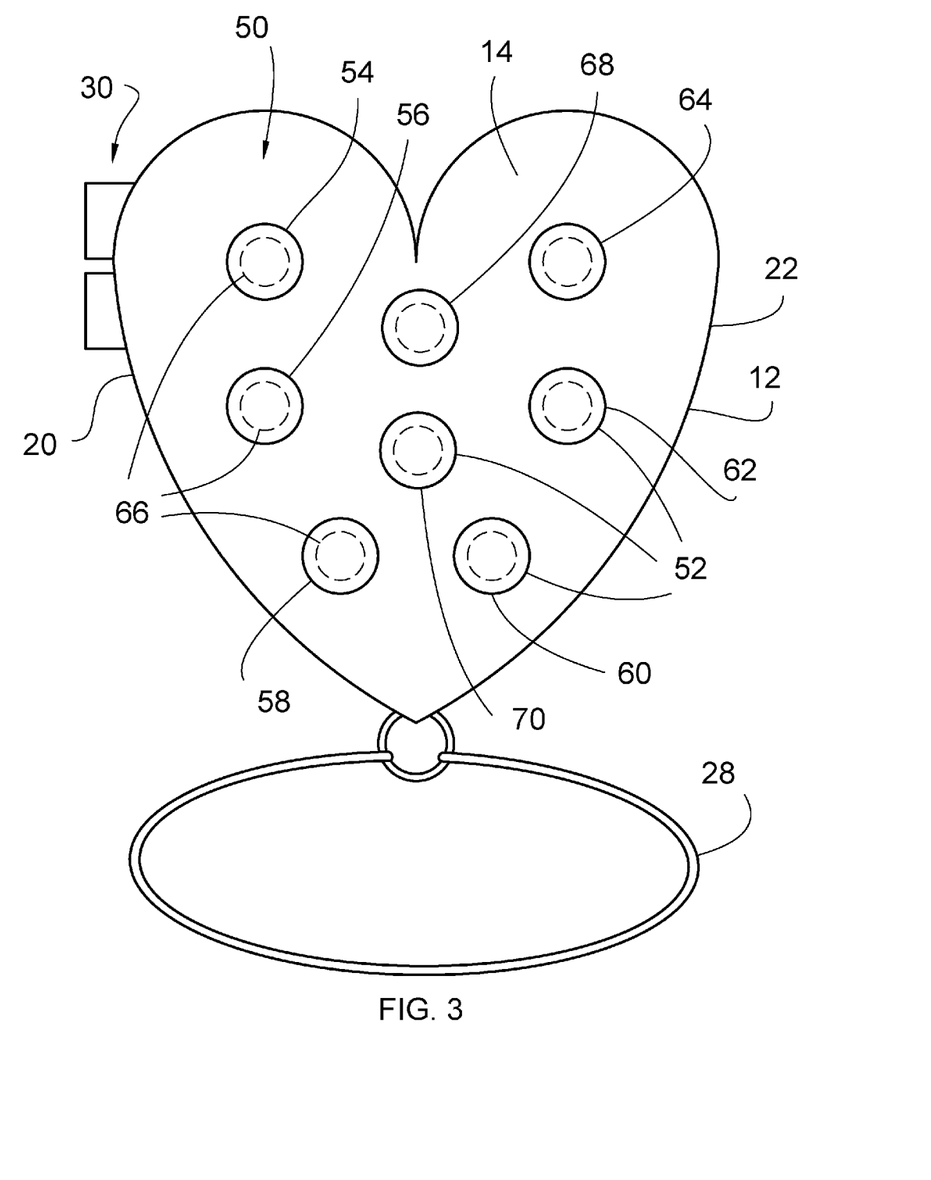
FIG. 3 is a top phantom view of an embodiment of the disclosure.
Figure 4:
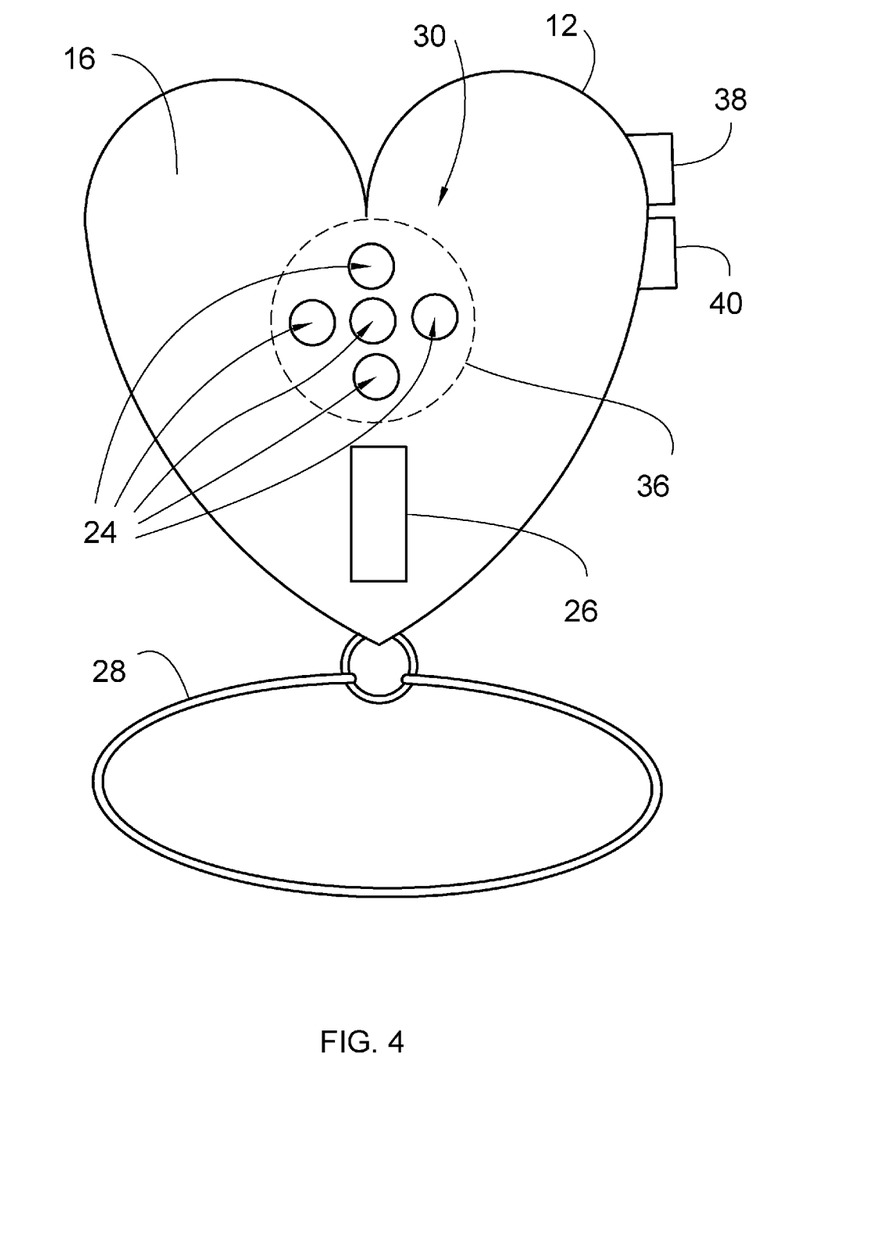
FIG. 4 is a phantom view of an embodiment of the disclosure.
Figure 5:
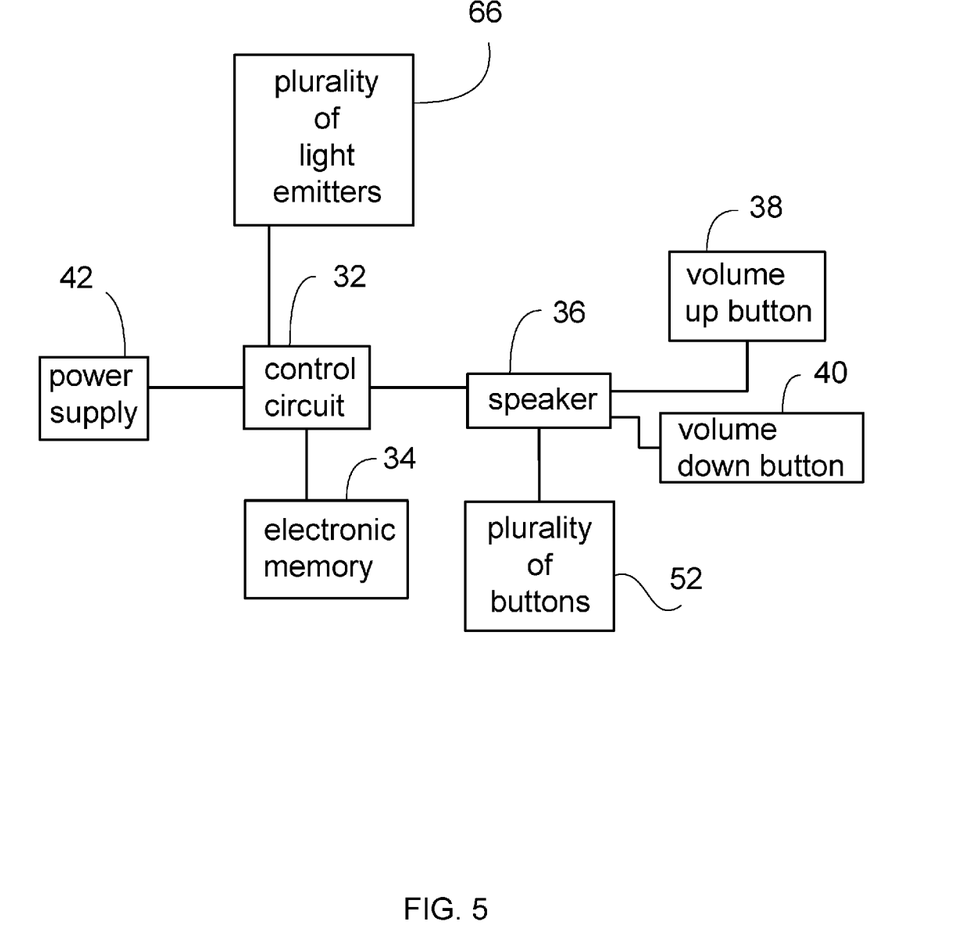
FIG. 5 is a schematic view of an embodiment of the disclosure.

With reference now to the drawings, and in particular to FIGS. 1 through 5 thereof, a new training device embodying the principles and concepts of an embodiment of the disclosure and generally designated by the reference numeral 10 will be described.

As best illustrated in FIGS. 1 through 5, the CPR training assembly 10 generally comprises a housing 12 that has a top wall 14, a bottom wall 16 and an exterior wall 18 extending therebetween. The exterior wall 18 has a first lateral surface 20 and a second lateral surface 22, and each of the first lateral surface 20 and the second lateral surface 22 is concavely arcuate with respect to a center line of the housing 12. Thus, the housing 12 has a heart shaped cross-section taken along a line extending through the top wall 14 and the bottom wall 16. The bottom wall 16 has a plurality of audio apertures 24 extending into an interior of the housing 12.

A clip 26 may be coupled to the housing 12 and for engaging an article of clothing, such as a shirt or the like. The clip 26 may comprise any mechanical clip 26 that can releasably engage clothing, such as an alligator clip 26 or the like. Additionally, a lanyard 28 may be coupled to the housing 12 thereby facilitating the housing 12 to be worn around a neck in the convention of a necklace. The clip 26 and the lanyard 28 facilitate the housing 12 to be carried without worry of losing the housing 12 in a chaotic environment.

An audio unit 30 is coupled to the housing 12 and emits audio outwardly therefrom for audibly alerting a user. The audio unit 30 stores data pertaining to audible instructions for performing CPR or choking rescue on infants, children and adults. The audio unit 30 comprises a control circuit 32 that is positioned within the housing 12 and electronic memory 34 that is positioned within the housing 12. The electronic memory 34 is electrically coupled the control circuit 32 and the electronic memory 34 stores a plurality of data sets. Each of the data sets pertains to a respective one of the audible instructions for CPR or choking rescue on infants, children or adults. The electronic memory 34 may comprise ROM memory, flash memory and any other type of electronic data storage. Additionally, the audible instructions may be recorded in the language that is common to the area in which the user will be carrying the housing 12.

A speaker 36 is positioned within the housing 12 and the speaker 36 is electrically coupled to the control circuit 32. The speaker 36 emits the audible instructions and the speaker 36 is aligned with the audio apertures 24 in the bottom wall 16 of the housing 12 to pass the audible instructions through the audio apertures 24. The speaker 36 may be an electronic speaker that has an operational noise level ranging between approximately 70.0 dBA and 100.0 dBA. In this way the audible instructions can be broadcast at a volume that is sufficiently high to overcome significant background noise. The speaker 36 may be a water resistant speaker or the like such that the speaker is not damaged by exposure to water or other electrically conductive liquids.

A volume up button 38 is movably coupled to the housing 12 and the volume up button 38 is electrically coupled to the control circuit 32. The volume up button 38 increases a volume of the speaker 36 when the volume up button 38 is manipulated. A volume down button 40 is movably coupled to the housing 12 and the volume down button 40 is electrically coupled to the control circuit 32. The volume down button 40 decreases the volume of the speaker 36 when the volume down button 40 is manipulated.

A power supply 42 is positioned within the housing 12 and the power supply 42 is electrically coupled to the control circuit 32. The power supply 42 comprises at least one battery 44 that is positioned within the housing 12. The at least one battery 44 is electrically coupled to the control circuit 32. The power supply 42 further comprises a charge port 46 that is recessed into the exterior wall 18 of the housing 12. The charge port 46 insertably receives a charge cord 48 from a power source, such as a battery charger or the like. The charge port 46 is electrically coupled to the at least one battery 44 for recharging the at least one battery 44. Additionally, the charge port 46 may be a micro usb port or any other conventional electrical port for charging a battery.

A control unit 50 is coupled to the housing 12 and the control unit 50 is electrically coupled to the audio unit 30. The control unit 50 is manipulated to select the audible instructions for a respective one of the infants, children and adults. In this way the user can select to receive audible instructions that correspond to whether an infant, a child or an adult needs CPR or choking rescue. Thus, the user can competently respond to a medical emergency when access to 911 or other emergency response is not available.

The control unit 50 comprises a plurality of buttons 52 and each of the buttons 52 is movably positioned on the top wall 14 of the housing 12. Each of the buttons 52 is electrically coupled to the control circuit 32 and each of the buttons 52 has one of the data sets in the electronic memory 34 associated therewith. The plurality of buttons 52 includes an infant choke button 54, an infant CPR button 56, a child choke button 58, a child CPR button 60, an adult choke button 62 and an adult CPR button 64. The electronic memory 34 communicates the associated data set to the speaker 36 when the associated button 52 is manipulated. In this way the speaker 36 emits audible instructions specifically for whether an infant, a child or an adult needs choking rescue or CPR.

A plurality of light emitters 66 is provided and each of the light emitter is coupled to the top wall 14 of the housing 12. Each of the light emitters 66 is positioned within the housing 12 and each of the light emitters 66 is aligned with a respective one of the buttons 52. Moreover, each of the light emitters 66 is electrically coupled to the control circuit 32. Each of the light emitters 66 is turned on when one of the buttons 52 is depressed thereby facilitating the plurality of buttons 52 to be illuminated. In this way the plurality of buttons 52 are visible to the user in a darkened environment.

The audible instructions for each of the data sets may be broken into a sequence of instructional steps for performing CPR or choking rescue. The sequence of instructional steps corresponding to the selected audible instructions is broadcast through the speaker 36 in chronological order for performing CPR or choking rescue. The plurality of buttons 52 additionally includes a repeat button 68 and a pause button 70. The pause button 70 pauses the broadcast of the selected audible instructions to give the user time to perform the actions prescribed by the audible instructions. The repeat button 68 repeats the sequence of instructional steps that has most recently been broadcast.

In use, a selected one of the buttons 52 is manipulated when the user needs to perform CPR or choking rescue. The speaker 36 broadcasts the audible instructions that correspond to whether an infant, a child or an adult needs CPR or choking rescue. In this way the user is instructed to provide competent emergency medical care when emergency responders are not available, such as areas experiencing military conflict, natural disasters and other emergencies that involve lack of professional medical help. The pause button 70 is manipulated at any selected time to pause the audible instructions. Additionally, the repeat button 68 is manipulated to repeat the most recently broadcast sequence of instructional steps.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. A CPR training assembly being configured to emit spoken instructions for performing CPR on an individual in an emergency situation, said assembly comprising:

a housing;

an audio unit being coupled to said housing and emitting audio outwardly therefrom wherein said audio unit is configured to audibly alert a user, said audio unit storing data pertaining to audible instructions for performing CPR or choking rescue on infants, children and adults; and a control unit being coupled to said housing, said control unit being electrically coupled to said audio unit such that said control unit selects said audible instructions for a respective one of the infants, children and adults wherein said control unit is configured to facilitate the user to receive audible instructions that correspond to whether an infant, a child or an adult needs CPR or choking rescue;

wherein said housing has a top wall, a bottom wall and an exterior wall extending there between, said exterior wall having a first lateral surface and a second lateral surface, each of said first lateral surface and said second lateral surface being concavely arcuate with respect to a center line of said housing such that said housing has a heart shaped cross-section taken along a line extending through said top wall and said bottom wall, said bottom wall having a plurality of audio apertures extending into an interior of said housing.

2. The assembly according to claim 1, wherein said audio unit comprises: a control circuit being positioned within said housing; and an electronic memory being positioned within said housing, said electronic memory being electrically coupled said control circuit, said electronic memory storing a plurality of data sets, each of said data sets pertaining to a respective one of the audible instructions for CPR or choking rescue on infants, children or adults.

3. The assembly according to claim 2, further comprising a speaker being positioned within said housing, said speaker being electrically coupled to said control circuit, said speaker emitting said audible instructions, said speaker being aligned with said audio apertures in said bottom wall of said housing to pass said audible instructions through said audio apertures.

4. The assembly according to claim 3, further comprising a volume up button being movably coupled to said housing, said volume up button being electrically coupled to said control circuit, said volume up button increasing a volume of said speaker when said volume up button is manipulated.

5. The assembly according to claim 3, further comprising a volume down button being movably coupled to said housing, said volume down button being electrically coupled to said control circuit, said volume down button decreasing a volume of said speaker when said volume down button is manipulated.

6. The assembly according to claim 2, further comprising a power supply being positioned within said housing, said power supply being electrically coupled to said control circuit.

7. The assembly according to claim 6, wherein said power supply comprises at least one battery being positioned within said housing, said at least one battery being electrically coupled to said control circuit.

8. The assembly according to claim 7, further comprising a charge port being recessed into said exterior wall of said housing wherein said charge port is configured to insertably receive a charge cord from a power source, said charge port being electrically coupled to said at least one battery for recharging said at least one battery.

9. The assembly according to claim 1, wherein said control unit comprises a plurality of buttons, each of said buttons being movably positioned on said top wall of said housing, each of said buttons being electrically coupled to said control circuit, each of said buttons having one of said data sets in said electronic memory being associated therewith.

10. The assembly according to claim 9, wherein said plurality of buttons includes an infant choke button, an infant CPR button, a child choke button, a child CPR button, an adult choke button and an adult CPR button, said electronic memory communicating said associated data set to said speaker when said associated button is manipulated wherein said speaker is configured to emit audible instructions specifically for whether an infant, a child or an adult needs choking rescue or CPR.

11. A CPR training assembly being configured to emit spoken instructions for performing CPR on an individual in an emergency situation, said assembly comprising:

a housing having a top wall, a bottom wall and an exterior wall extending therebetween, said exterior wall having a first lateral surface and a second lateral surface, each of said first lateral surface and said second lateral surface being concavely arcuate with respect to a center line of said housing such that said housing has a heart shaped cross-section taken along a line extending through said top wall and said bottom wall, said bottom wall having a plurality of audio apertures extending into an interior of said housing;

an audio unit being coupled to said housing and emitting audio outwardly therefrom wherein said audio unit is configured to audibly alert a user, said audio unit storing data pertaining to audible instructions for performing CPR or choking rescue on infants, children and adults, said audio unit comprising:

a control circuit being positioned within said housing; an electronic memory being positioned within said housing, said electronic memory being electrically coupled said control circuit, said electronic memory storing a plurality of data sets, each of said data sets pertaining to a respective one of the audible instructions for CPR or choking rescue on infants, children or adults; a speaker being positioned within said housing, said speaker being electrically coupled to said control circuit, said speaker emitting said audible instructions, said speaker being aligned with said audio apertures in said bottom wall of said housing to pass said audible instructions through said audio apertures; a volume up button being movably coupled to said housing, said volume up button being electrically coupled to said control circuit, said volume up button increasing a volume of said speaker when said volume up button is manipulated;

a volume down button being movably coupled to said housing, said volume down button being electrically coupled to said control circuit, said volume down button decreasing a volume of said speaker when said volume down button is manipulated; and a power supply being positioned within said housing, said power supply being electrically coupled to said control circuit, said power supply comprising:

at least one battery being positioned within said housing, said at least one battery being electrically coupled to said control circuit; and a charge port being recessed into said exterior wall of said housing wherein said charge port is configured to insertably receive a charge cord from a power source, said charge port being electrically coupled to said at least one battery for recharging said at least one battery; and a control unit being coupled to said housing, said control unit being electrically coupled to said audio unit such that said control unit selects said audible instructions for a respective one of the infants, children and adults wherein said control unit is configured to facilitate the user to receive audible instructions that correspond to whether an infant, a child or an adult needs CPR or choking rescue, said control unit comprising a plurality of buttons, each of said buttons being movably positioned on said top wall of said housing, each of said buttons being electrically coupled to said control circuit, each of said buttons having one of said data sets in said electronic memory being associated therewith, said plurality of buttons including an infant choke button, an infant CPR button, a child choke button, a child CPR button, an adult choke button and an adult CPR button, said electronic memory communicating said associated data set to said speaker when said associated button is manipulated wherein said speaker is configured to emit audible instructions specifically for whether an infant, a child or an adult needs choking rescue or CPR.

\* \* \* \* \*